United States Patent

Doyle

[11] Patent Number: 5,810,582
[45] Date of Patent: Sep. 22, 1998

[54] ORTHODONTIC BRACKET HOLDING AND PLACEMENT APPARATUS

[76] Inventor: Walter A. Doyle, 1088 Nicklaus Ct., Lexington, Ky. 40511

[21] Appl. No.: 674,456

[22] Filed: Jul. 2, 1996

[51] Int. Cl.[6] ....................................................... A61C 7/00
[52] U.S. Cl. .................................... 433/4; 433/9; 206/369
[58] Field of Search ........................ 433/3, 4, 9; 206/570, 206/368, 369, 63.5, 564

[56] References Cited

U.S. PATENT DOCUMENTS

| | | | |
|---|---|---|---|
| 4,050,894 | 9/1977 | Genis | 206/368 |
| 4,978,007 | 12/1990 | Jacobs et al. | 206/469 |
| 5,354,199 | 10/1994 | Jacobs et al. | 433/9 |

*Primary Examiner*—Gary E. O'Connor
*Attorney, Agent, or Firm*—Emrich & Dithmar

[57] ABSTRACT

Apparatus for holding and installing a plurality of orthodontic brackets on a patient's teeth includes an opaque housing having a plurality of spaced slots each adapted to receive a pliers, or tweezers, of the "reverse locking" type, where each pliers engages and supports a respective orthodontic bracket. Attached to the user engaging end, or handle, of each pliers is an opaque silicone cap which facilities gripping the pliers, maintains the pliers securely in position in the housing, and forms an airtight seal about each slot in the housing. Applied to each orthodontic bracket is a light-curable composite bonding material which is maintained in position within a respective slot in spaced relation from the housing. The bracket installer grasps a silicone cap in removing the pliers and orthodontic bracket combination from the housing and affixes the bracket to an intended tooth by means of the bonding material. With the housing providing a sealed enclosure and each slot sealed in an airtight manner by a respective pliers cap, an inert gas may be injected into the housing to preserve the bonding material over an extended storage period. The housing includes connected upper and lower members which can be separated to allow for recovery of dropped brackets, cleaning of the housing, and sterilization. The orthodontic bracket holding and placement apparatus simplifies and substantially reduces the number of steps involved in installing orthodontic brackets as well as the time required.

16 Claims, 2 Drawing Sheets

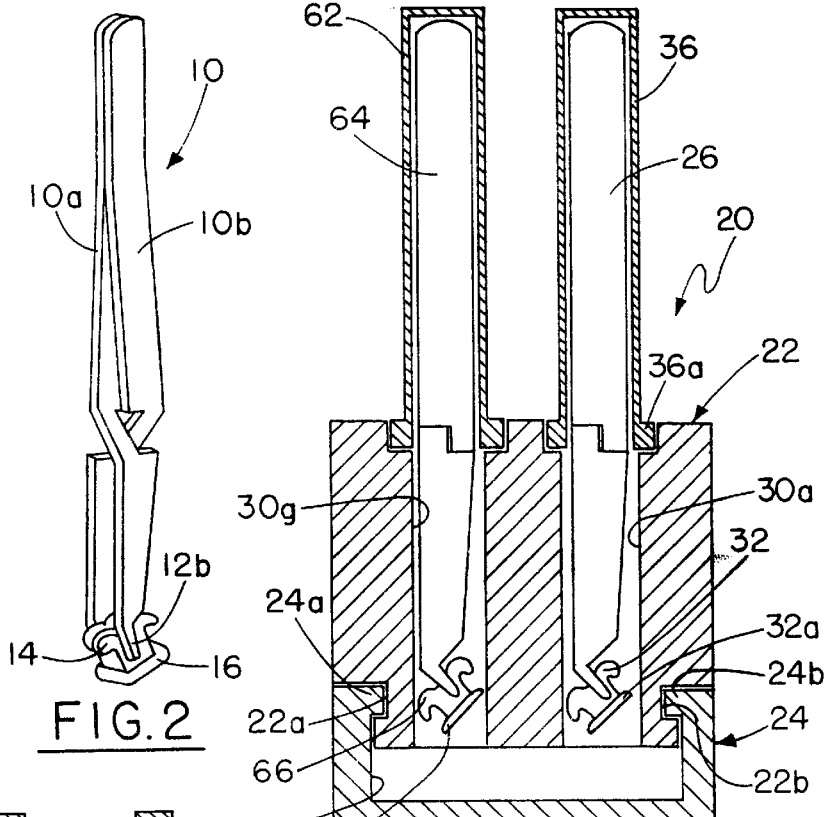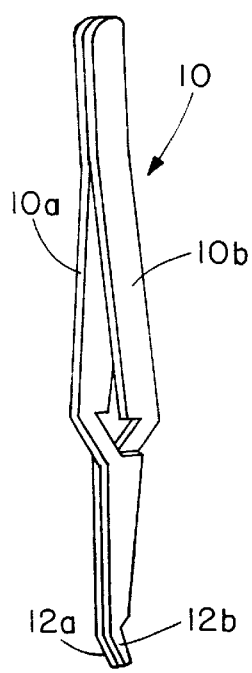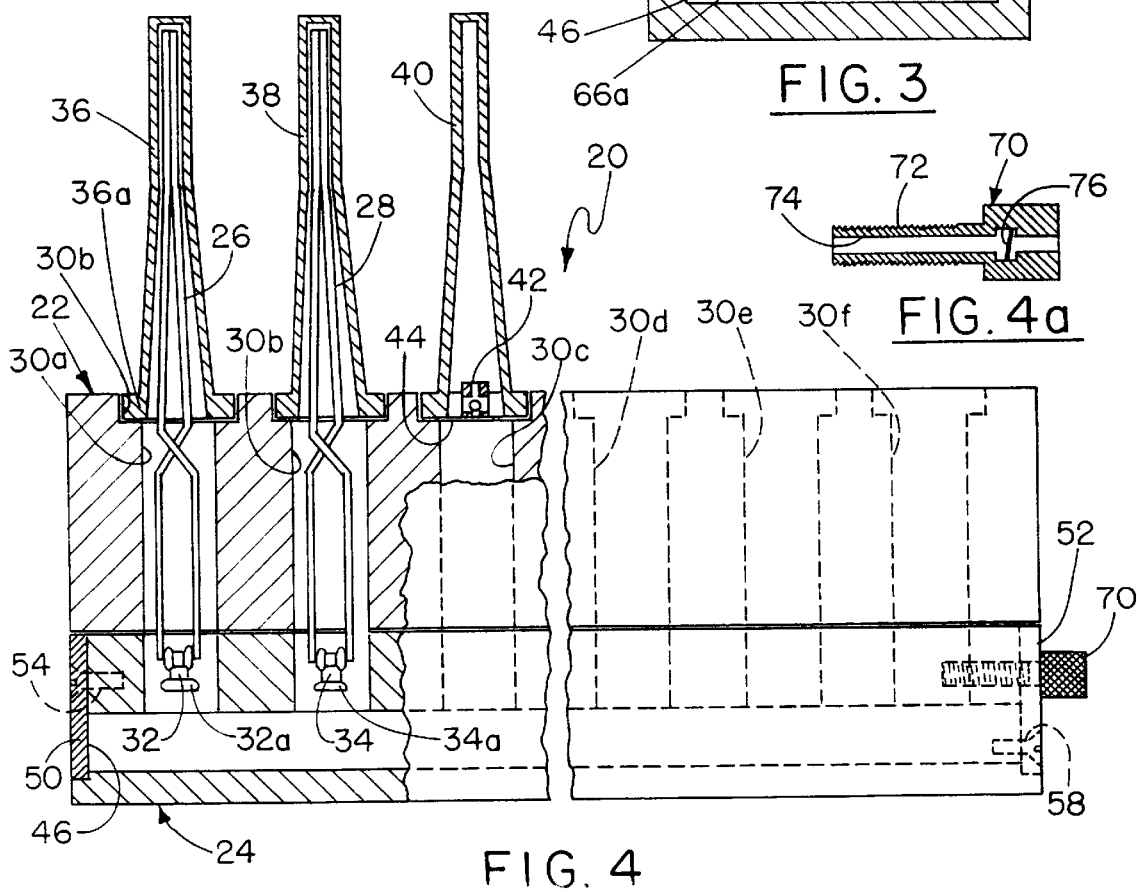

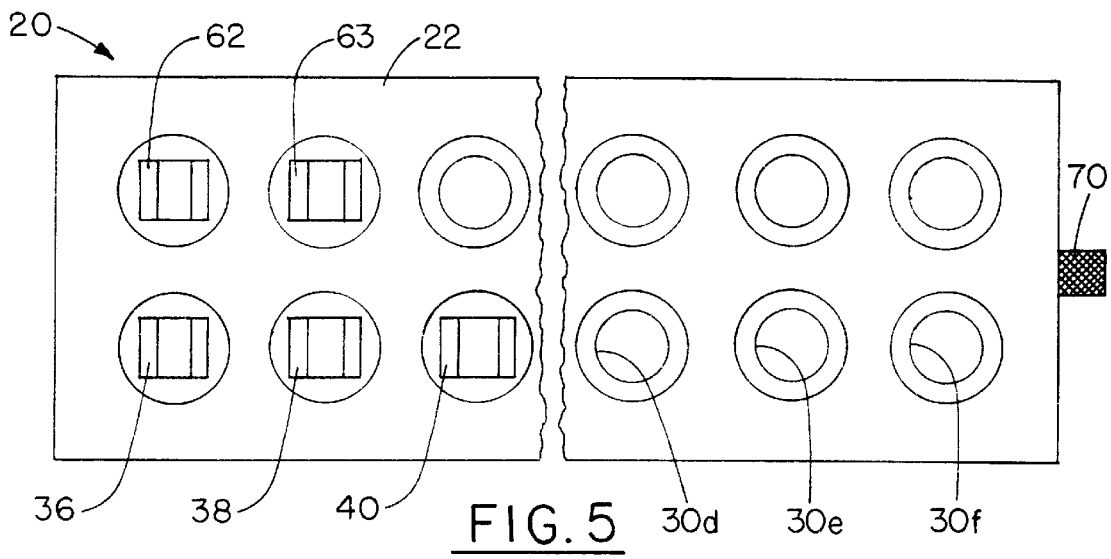
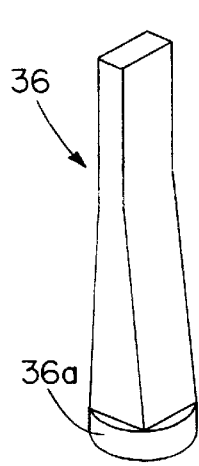
FIG. 6
FIG. 6a
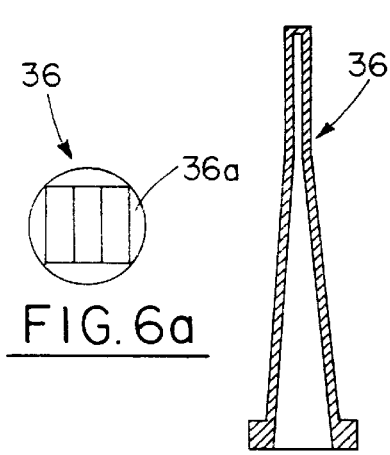
FIG. 7
FIG. 8
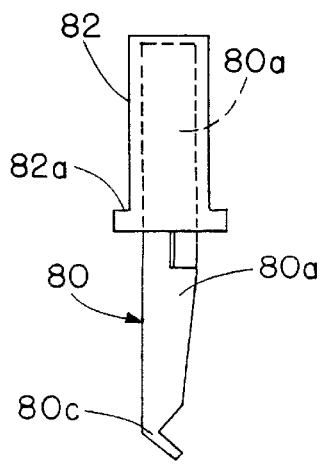
FIG. 9
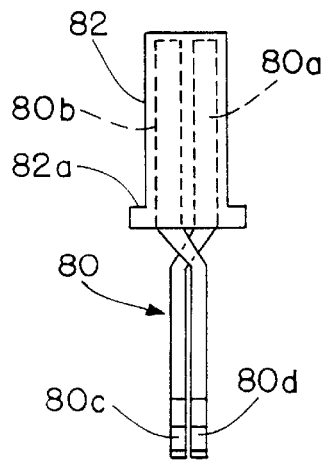
FIG. 10
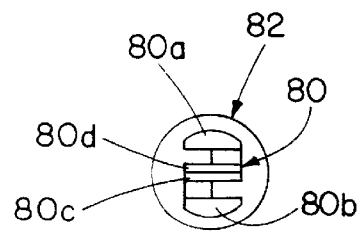
FIG. 11

5,810,582

ORTHODONTIC BRACKET HOLDING AND PLACEMENT APPARATUS

FIELD OF THE INVENTION

This invention relates generally to orthodontics and is particularly directed to apparatus for storing and installing orthodontic brackets on a patient's teeth.

BACKGROUND OF THE INVENTION

Orthodontic braces comprised of a plurality of brackets and an arch wire for applying the appropriate force to a patient's teeth are commonly used to move the teeth into a desired configuration or alignment. Each bracket is firmly attached to its associated tooth and serves as a handle on the tooth for the force producing arch wire. The need for accurate, efficient orthodontic bracket placement has stimulated the development of various procedures and extensive instrumentation in an attempt to achieve optimum clinical results for the patient.

Two basic procedures in the placement of orthodontic brackets have evolved and are known respectively as the direct and indirect approaches. Direct bracket placement is the most popular because of the apparent reduced cost and the elimination of laboratory work which is required with the indirect procedure. However, the indirect bracket placement procedure generally affords greater bracket positioning accuracy and is more easily delegated by the orthodontic practitioner. Continuing efforts to improve the accuracy and efficiency of the direct placement procedure has lead to the development of such items as bracket markers, pliers, gauges and prepasted brackets. However, there is still considerable inefficiency and positioning inaccuracy inherent in the direct bracket placement procedure.

The typical direct bracket application procedure involves the following steps in sequence:

1. The teeth are etched and prepared for bracketing.
2. A bracket is engaged and picked up using a bracket pliers.
3. A bonding composite material is applied to the bracket.
4. The orthodontic bracket is applied, or attached, to the tooth.
5. A bracket gauge is picked up and used to check the bracket height.
6. Angulation is checked and adjusted using an instrument or explorer.
7. Excess composite bonding material is removed.
8. The composite bonding material is light-cured.
9. The last seven steps are repeated 19 more times, or 27 more times if the patient's molars are bracketed.

This multi-step procedure is complex and time consuming and typically requires the assistance of a second person. Even with this detailed procedure, accurate positioning of a bracket on each tooth is difficult and requires considerable skill.

The present invention addresses the problems inherent in the prior art direct bracket placement procedure by providing an orthodontic bracket holding and placement apparatus which substantially simplifies and shortens the bracket application procedure by reducing the number of steps involved, permitting one person to easily and accurately install brackets on each tooth, and permits a composite bonding material to be pre-applied to each bracket in an arrangement which is adapted for shipment and for storage for an extended period.

OBJECTS AND SUMMARY OF THE INVENTION

Accordingly, it is an object of the present invention to provide an improved packaging and installation arrangement for orthodontic brackets.

Another object of the present invention is to provide an orthodontic bracket holding and placement apparatus for storing a plurality of orthodontic brackets, each of which is coupled to and supported by a bracket placement instrument which is adapted for use with virtually every type of bracket in current use.

Yet another object of the present invention is to provide a closed, light-proof housing for shipping and storing for an extended period orthodontic brackets having a light-cured adhesive affixed thereto.

A further object of the present invention is to facilitate the attachment of orthodontic brackets to a patient's teeth which permits more accurate positioning of each bracket on a respective tooth in less time using only one hand.

A still further object of the present invention is to provide an improved procedure for installing orthodontic brackets on a patient's teeth which is faster and more accurate than prior approaches and which can be more easily performed by a single person.

This invention contemplates apparatus for holding and attaching a plurality of orthodontic brackets to respective teeth of a patient, wherein each orthodontic bracket includes an adhesive deposit attached thereto for affixing the bracket to a respective tooth, the apparatus comprising a housing of an opaque material and having a plurality of spaced elongated, linear slots each defined by an opening in said housing; a plurality of pliers each engaging a respective one of the orthodontic brackets and disposed within a respective slot of the housing; a plurality of opaque covers each engaging a respective one of the pliers and attached to the housing and disposed over a respective slot therein for maintaining an orthodontic bracket in fixed position within a slot and preventing the adhesive deposit attached to each orthodontic bracket from being exposed to light as well as from contacting the housing.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

FIG. 1 is a perspective view of a tweezers or pliers for use in engaging and supporting an orthodontic bracket in the orthodontic bracket holding and placement apparatus of the present invention;

FIG. 2 is a perspective view of the pliers shown in FIG. 1 illustrating the manner in which the pliers engages an orthodontic bracket to which is applied an adhesive deposit;

FIG. 3 is a transverse sectional view of an orthodontic bracket holding and placement apparatus illustrating the positioning of two orthodontic brackets within the apparatus in accordance with the principles of the present invention;

FIG. 4 is a longitudinal sectional view shown partially in phantom of the orthodontic bracket holding and placement apparatus of the present invention;

FIG. 4a is a longitudinal sectional view of a valve assembly for use in one embodiment of the orthodontic bracket holding and placement apparatus of the present invention;

FIG. 5 is a partial top plan view of the orthodontic bracket holding and placement apparatus of the present invention showing a plurality of spaced slots in the housing, each adapted to receive a respective orthodontic bracket engaging pliers;

FIGS. 6 and 6a are respectively perspective and end-on plan views of a pliers cap or cover for use in the present invention;

FIGS. 7 and 8 are longitudinal sectional views of the pliers cover shown in FIG. 6;

FIGS. 9 and 10 are side elevation views shown partially in phantom of another embodiment of an orthodontic bracket engaging pliers for use in the present invention; and FIG. 11 is an end-on view of the orthodontic bracket engaging pliers shown in FIGS. 9 and 10.

DETAILED DESCRIPTION OF THE PREFERRED EMBODIMENTS

Referring to FIG. 1, there is shown a perspective view of a pliers, or tweezers, 10 for use in the orthodontic bracket holding and placement apparatus of the present invention. Pliers 10 is shown in FIG. 2 engaging an orthodontic bracket 14 having an adhesive deposit 16 in the form of a bonding composite material applied thereto. The adhesive deposit 16, which preferably is light-curable, allows the orthodontic bracket 14 to be securely affixed to a patient's tooth (not shown in the figures for simplicity).

Pliers 10 is of the "reverse locking" type and includes first and second handles 10a and 10b. Pliers 10 is preferably comprised of stainless steel. The first and second handles 10a and 10b are securely attached to one another at respective adjacent ends thereof, with the opposed ends of the handles freely displaceable relative to one another. The free ends of each of the first and second handles 10a, 10b are provided with respective gripping elements 12a and 12b for engaging the orthodontic bracket 14. By grasping an intermediate portion of the handles 10a, 10b and applying opposed, inwardly directed forces to the two handles, the gripping elements 12a, 12b can be displaced apart from one another for engaging and holding orthodontic bracket 14. The pliers 10 as thus far described is conventional in design and operation and is well known in the relevant arts.

Referring to FIG. 3, there is shown a transverse sectional view of an orthodontic bracket holding and placement apparatus 20 in accordance with the principles of the present invention. A longitudinal sectional view shown partially in phantom of the orthodontic bracket holding and placement apparatus 20 of FIG. 3 is shown in FIG. 4. A partial top plan view of the orthodontic bracket holding and placement apparatus 20 is shown in FIG. 5. For simplicity, the inventive orthodontic bracket holding and placement apparatus 20 will henceforth be referred to as an orthodontic bracket carrier, or caddie.

The orthodontic bracket carrier 20 is generally box-like in shape and is preferably comprised of a lightweight, inexpensive material such as plastic which is opaque to light. Bracket carrier 20 includes an upper housing 22 and a lower housing 24 connected together in a manner described below. The upper housing 22 includes a plurality of elongated, cylindrical slots some of which are shown as elements 30a–30g in the figures. The lower ends of each of the cylindrical slots 30a–30g in the upper housing 22 terminate in a cavity, or chamber, 46 in the lower portion of carrier 20. Each of the aforementioned slots is adapted to receive a respective orthodontic bracket engaging pliers. Thus, pliers 26, 28 and 64 are respectively shown inserted in elongated slots 30a, 30b and 30g in upper housing 22. Pliers 26, 28 and 64 are respectively shown engaging and supporting orthodontic brackets 32, 34 and 66. Respectively affixed to orthodontic brackets 32, 34 and 66 are adhesive deposits 32a, 34a and 66a, each of which is preferably comprised of a composite bonding material.

In order to securely support each pliers in a fixed position within the orthodontic bracket carrier 20 and to prevent the light-curable bonding composite material, or adhesive, affixed to each orthodontic bracket from being exposed to light, a cover, or cap, is affixed to each pliers. Thus, covers 36, 38 and 62 are respectively attached to upper portions of pliers 26, 28 and 64. A perspective view of pliers cover 36 is shown in FIG. 6, while FIGS. 6a, 7 and 8 respectively illustrate top plan and first and second longitudinal sectional views of the pliers cover. Pliers cover 36 is preferably comprised of silicone which is opaque to light and thus prevents light from being incident upon and curing the adhesive deposits on each of the orthodontic brackets within the orthodontic bracket carrier 20. Cover 36 includes a peripheral lip, or shoulder, 36a disposed about its open end. The open end of cover 36 is adapted to receive the connected end portions of the pair of handles of a pliers as shown in the figures. The cover's peripheral lip 36a is adapted for positioning in a respective recessed portion at the upper end of a slot in the orthodontic bracket carrier 20. Thus, as shown in FIG. 4, the peripheral lip 36a of pliers cover 36 is inserted in the upper end, recessed portion 30b of slot 30a within orthodontic bracket carrier 20. Cover 36 is inserted in recessed portion 30b in a tight fitting manner so as to maintain pliers 26 securely in a fixed position within the orthodontic carrier bracket 20. The combination of orthodontic bracket 32 and adhesive deposit 32a affixed thereto is also securely maintained in fixed position within the slot 30a in the orthodontic bracket carrier 20. In this manner, the adhesive deposit 32a is prevented from contacting the inner portion of the orthodontic bracket carrier 20 defining slot 30a therein. Fabricating the pliers covers from silicone allows a tight seal to be formed where the cover is positioned on and engages the upper portion of the orthodontic bracket carrier 20 to prevent light and air from entering the carrier. Silicone also provides the required flexibility and resilience to permit the application of a squeezing force on the pliers within the cover to open the pliers when engaging or releasing an orthodontic bracket. The preferred silicone composition of the pliers covers is also capable of undergoing conventional sterilization procedures and can be colored-coded for identifying the individual tooth with which the orthodontic bracket attached to the pliers within the cover is intended to be used. The size of the inner portion of each cover may be selected so as to securely and intimately engage the end of a pliers and to prevent removal of the pliers from the cover. In another embodiment, a conventional adhesive may be used to securely bond a pliers with its associated cover.

The carrier's upper housing 22 and lower housing 24 are adapted for sliding engagement with one another. Thus, upper housing includes first and second slots, or recesses, 22a and 22b in opposed lateral surfaces thereof. Similarly, lower housing 24 includes facing first and second inwardly directed shoulders 24a and 24b. The first and second opposed slots 22a, 22b in the upper housing 22 are respectively adapted to receive the first and second inwardly directed opposed shoulders 24a, 24b of the lower housing 24. With the upper and lower housings 22, 24 coupled together in a sliding manner as described, opposed ends of these housings are adapted to receive first and second end plates, or brackets, 50 and 52. End plates 50, 52 each include a respective aperture therein for receiving threaded couplers 54 and 58. Threaded couplers, or screws, 54 and 58 are respectively inserted through the first and second end plates 50 and 52 and engage adjacent portions of the upper and lower housings 22, 24. The first and second end plates 50, 52 in combination with the pliers covers inserted over and covering the slots within the upper housing 22 form a closed, sealed compartment within the orthodontic bracket carrier 20. Seal elements such as comprised of rubber may be used to form leak proof seals between the end plates 50 and 52 and the carrier housings.

Also inserted through the second end plate 52 and through an adjacent portion of the upper housing 22 is a third threaded coupler 70. A sectional view of the third threaded coupler 70 is shown in FIG. 4a. Coupler 70 includes an outer threaded portion 72 and an inner channel, or duct, 74 extending the length thereof. Disposed within the coupler's inner channel 74 is a valve 76. The valve 76 permits an inert gas, such as argon, nitrogen, or $CO_2$ to be directed into the orthodontic bracket carrier 20 and prevents its escape from the carrier. An inert gas may be directed into the orthodontic bracket carrier 20 to preserve the adhesive deposits disposed on each of the orthodontic brackets by retarding their curing and other chemical changes, permitting the orthodontic bracket and adhesive deposit combinations to be stored for extended periods of time within the orthodontic bracket carrier 20. In another embodiment, an inert gas may be stored in a cover 40 in which a pliers is not inserted. Cover 40, which also is preferably comprised of silicone, is provided with a sealed lower end portion including the combination of a wall, or partition, 44 and a valve 42. Silicone cover 40 may be filled with an inert gas which can be discharged via valve 42 into the orthodontic bracket carrier 40 for preserving the adhesive deposits attached to each of the orthodontic brackets therein. The sealed contact between the cover 40 and the top portion of the upper housing 22 about slot 30c therein, in combination with the unidirectional characteristics of valve 42, prevent the escape of the inert gas injected into the orthodontic bracket carrier 20.

Referring to FIG. 9, there is shown another embodiment of the combination of a pliers 80 and cover 82 for use in the orthodontic bracket holding and placement apparatus of the present invention. Pliers 80 includes first and second handles 80a and 80b which are connected adjacent their center portions to provide the pliers with a "reverse locking" feature. Adjacent ends of the first and second handles 80a, 80b include respective gripping elements 80c and 80d for engaging an orthodontic bracket which is not shown in the figures for simplicity. Disposed about and engaging adjacent second ends of each of the handles 80a, 80b is a pliers cover 82 which includes a peripheral lip 82a disposed about its open end which is adapted to receive the pliers 80. In this embodiment, the pliers cover 82 is fabricated as an integral part of the pliers 80 to permit the cover to provide a "spring force" on the first and second handles 80a, 80b. This arrangement allows the use of a large variety of materials other than the stainless steel used in the previously described embodiment of the pliers. Also in this embodiment, cover 82 is bonded to the first and second handles 80a, 80b of the pliers 80 by means of a conventional adhesive which is not shown in the figures for simplicity.

There has thus been shown apparatus for holding, storing and installing a plurality of orthodontic brackets on a patient's teeth. The apparatus includes an opaque housing having a plurality of spaced slots each adapted to receive a "reverse locking" pliers. Each pliers engages and supports a respective orthodontic bracket to which is applied an adhesive deposit in the form of a composite bonding material. Disposed over the handle portion of the pliers is an opaque cover, or cap, which may be comprised of silicone and which facilitates gripping the pliers, maintains the pliers securely in position in the housing, and forms an air tight and light tight seal about each slot when its associated pliers is inserted in the slot within the housing. The composite bonding material is light curable and is shielded from light when in the housing by the housing itself as well as by the pliers cover. The lower peripheral lip of each pliers cover is inserted in a groove disposed about the upper end of each slot so as to securely maintain the pliers and pliers cover combination in fixed position in the housing. By maintaining the pliers in fixed position within the housing, the composite bonding material deposited on an orthodontic bracket engaged and supported by the pliers is prevented from engaging the wall portion of the housing defining the slot. The orthodontic bracket installer grasps the pliers cover, removing the pliers and orthodontic bracket combination from the housing, and affixes the bracket to an intended tooth by means of the composite bonding material. With the housing providing a sealed enclosure and each slot sealed in an airtight manner by a respective pliers cover, an inert gas may be injected into the housing to preserve the composite bonding material over an extended storage period. The housing includes connected upper and lower housing members which may be separated to allow for recovery of dropped brackets, as well as for cleaning and sterilization of the housing. The orthodontic bracket holding and placement apparatus simplifies and substantially reduces the number of steps involved in as well as the time required for installing the orthodontic brackets.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

I claim:

1. Apparatus for holding and attaching a plurality of orthodontic brackets to respective teeth of a patient, wherein each orthodontic bracket includes an adhesive deposit attached thereto for affixing the bracket to a respective tooth, said apparatus comprising:

a housing comprised of an opaque material and having a plurality of spaced elongated, linear slots each defined by an opening in said housing;

a plurality of pliers each adapted for engaging a respective one of said orthodontic brackets and disposed within a respective slot of said housing; and a plurality of opaque cover means each engaging a respective one of said pliers and attached to said housing and disposed over a respective slot therein for maintaining an orthodontic bracket in fixed position within a slot and preventing the adhesive deposit attached to each orthodontic bracket from being exposed to light as well as from contacting said housing.

2. The apparatus of claim 1 wherein each cover means includes a peripheral lip on an open end thereof, and wherein said housing further includes a plurality of recessed portions each disposed about a respective slot, and wherein each peripheral lip of a cover means is inserted in a tight fitting manner within a respective recessed portion about a slot.

3. The apparatus of claim 2 wherein said recessed portions are in an upper portion of said housing and said slots extend downward into said housing.

4. The apparatus of claim 1 wherein each of said pliers is of the reverse locking type.

5. The apparatus of claim 4 wherein each of said pliers is comprised of stainless steel.

6. The apparatus of claim 1 wherein each of said cover means is comprised of silicone.

7. The apparatus of claim 1 wherein said opaque material is plastic.

8. The apparatus of claim 1 further comprising means for directing an inert gas into said housing and said slots therein for inhibiting curing and other chemical changes of the adhesive deposits.

9. The apparatus of claim 8 wherein said means for directing an inert gas into said housing includes a valve connected to and extending into said housing.

10. The apparatus of claim 8 wherein said means for directing an inert gas into said housing includes one of said cover means disposed in a sealed manner over one of the slots and filled with an inert gas, said one of said cover means including a valve for permitting discharge of the inert gas into said one of the slots.

11. The apparatus of claim 8 wherein said inert gas is argon, nitrogen or $CO_2$.

12. The apparatus of claim 1 wherein each of said pliers and cover means is formed integrally with one another, and wherein said cover means urges said pliers to a configuration in secure engagement with a respective orthodontic bracket.

13. The apparatus of claim 1 wherein said housing includes an upper housing portion including said plurality of slots and a lower housing portion including an inner cavity connected to and continuous with said slots.

14. The apparatus of claim 13 further comprising coupling means for connecting said upper and lower housing portions in a sealed, sliding manner.

15. The apparatus of claim 1 wherein said cover means are color-coded to indicate to which tooth each orthodontic bracket is to be affixed.

16. Apparatus for holding a plurality of orthodontic brackets and for attaching each bracket to a respective tooth of a patient, said apparatus comprising:

a plurality of adhesive deposits each disposed on a respective orthodontic bracket:

a plurality of pliers each comprised of a handle portion and an engaging portion, wherein each pliers is adapted for engaging a respective orthodontic bracket;

a plurality of opaque caps each disposed over a respective pliers, each of said caps including an open end portion for receiving the handle portion of a pliers; and an opaque housing having a plurality of slots and a plurality of recessed portions disposed about an open end of each of said slots, wherein each pliers is disposed in a respective slot and each recessed portion is adapted to receive an open end portion of a cap in a tightfitting, sealed manner for preventing light from entering said housing and for securely maintaining each of said orthodontic bracket and adhesive deposit combinations in fixed position with a given slot.

* * * * *